(12) United States Patent
Foroni et al.

(10) Patent No.: US 9,993,340 B2
(45) Date of Patent: Jun. 12, 2018

(54) MOULD AND ACCESSORIES THEREOF DESTINED FOR THE FORMING OF AN ORTHOPEDIC MODULAR SPACER

(71) Applicant: G21 S.R.L., San Possidonio (MO) (IT)

(72) Inventors: Filippo Foroni, Mirandola (IT); Riccardo Ferrotto, Villar Perosa (IT); Michele Ferrotto, Pinerolo (IT)

(73) Assignee: G21 S.R.L., San Possidonio (IT)

( * ) Notice: Subject to any disclaimer, the term of this patent is extended or adjusted under 35 U.S.C. 154(b) by 0 days. days.

(21) Appl. No.: 15/230,995

(22) Filed: Aug. 8, 2016

(65) Prior Publication Data
US 2017/0333191 A1 Nov. 23, 2017

(30) Foreign Application Priority Data
May 17, 2016 (IT) .......... 102016000050387

(51) Int. Cl.
| | | |
|---|---|---|
| *B29C 33/40* | (2006.01) | |
| *B28B 7/34* | (2006.01) | |
| *A61F 2/30* | (2006.01) | |
| *B28B 7/00* | (2006.01) | |

(52) U.S. Cl.
CPC .............. *A61F 2/3094* (2013.01); *B28B 7/00* (2013.01); *A61F 2250/0059* (2013.01); *B28B 7/0029* (2013.01); *B28B 7/348* (2013.01); *B29C 33/405* (2013.01)

(58) Field of Classification Search
CPC ....... B29C 33/38; B29C 33/40; B29C 33/405; B28B 7/0029; B28B 7/348; A61F 2/3094
See application file for complete search history.

(56) References Cited

U.S. PATENT DOCUMENTS

| | | | | |
|---|---|---|---|---|
| 6,155,812 A | * | 12/2000 | Smith | ................ A61F 2/30942 249/141 |
| 6,361,731 B1 | | 3/2002 | Smith et al. | |
| 7,637,729 B2 | * | 12/2009 | Hartman | ................... A61F 2/30 249/102 |
| 7,789,646 B2 | | 9/2010 | Haney et al. | |
| 8,480,389 B2 | | 7/2013 | Haney et al. | |
| 8,801,983 B2 | | 8/2014 | Haney et al. | |
| 2009/0146342 A1 | | 6/2009 | Haney et al. | |
| 2009/0157189 A1 | | 6/2009 | Hartman et al. | |
| 2010/0292803 A1 | | 11/2010 | Giori | |
| 2010/0297276 A1 | | 11/2010 | Haney et al. | |
| 2013/0210952 A1 | * | 8/2013 | Wiesmayer | ............. B29C 33/40 521/189 |
| 2013/0344186 A1 | | 12/2013 | Haney et al. | |
| 2016/0129610 A1 | | 5/2016 | Cappelletti | |

FOREIGN PATENT DOCUMENTS

WO     2009073781 A2     6/2009

\* cited by examiner

*Primary Examiner* — James P Mackey
(74) *Attorney, Agent, or Firm* — Pearne & Gordon LLP

(57) ABSTRACT

A mold (1) and accessories thereof for the forming of an orthopedic spacer made of medical cement, defining a molding cavity (2) delimited by a molding surface (3) configured to impart a pre-established shape to the medical cement and to create the orthopedic spacer, wherein at least one sector (6) of the forming mold (1) defining at least one portion of the molding surface (3) is made with a thermoplastic copolymer based material.

20 Claims, 9 Drawing Sheets

MOULD AND ACCESSORIES THEREOF DESTINED FOR THE FORMING OF AN ORTHOPEDIC MODULAR SPACER

FIELD OF THE INVENTION

The present invention relates to a mould for the forming of an orthopaedic temporary spacer made of medical cement.

In particular, the present invention relates to a forming mould for the creation of orthopaedic temporary spacers made of medical cement.

DESCRIPTION OF RELATED ART

Orthopaedic temporary spacers are used to assist the treatment of prosthetic joint infections and septic arthritis with medical cement with, for example, one or more antibiotics added.

Various techniques are known in the state of the art for making orthopaedic spacers to be used in surgical operations.

In one case, the creation of orthopaedic spacers through a manual operation performed by specialist personnel directly in the operating theatre is known, by modelling and compacting the mass of medical cement so as to give it a shape similar to the joint structures (hip, knee and shoulder) where the infection is present.

In a different case, preformed spacers are made directly in the factory, by a company specialising in medical products. The resulting temporary spacer has reasonable mechanical resistance and allows the controlled release of the antibiotic "in situ".

A further and different case, now regarding the most common type of product and technique used in this field, relates to known moulds for the forming of orthopaedic temporary spacers that comprise at least two moulding shells to be coupled to one another for consolidating and giving shape to the medical cement introduced between them. Generally, the medical cement is inserted into the closed mould, i.e. with the moulding shells coupled, via a hole through which a dispenser is pushed once since the cement has a soft consistency. The moulding shells may be made of a semi-rigid material and may have the most varied of shapes precisely for making a spacer that can be adapted to the shoulder, knee or hip joints.

In particular, the moulding shells may be of a specular shape or may have a shape that allows mould couplings of the male-female type between one shell and the other.

The closing and/or pressing process of the shells according to the state of the art may be performed by specialist personal through a manual process or with the aid of a pressing tool that offers greater compacting efficacy of the cement and sealing of the mould shells.

In the state of the art the moulds for the forming of orthopaedic spacers are made of flexible materials in part so as to facilitate the aforementioned closing operations, both manual and using pressing tools, in part so as to facilitate the extraction of the spacer once it has set and is consolidated in the pre-established shape. For that purpose, forming moulds are known that have at least the moulding shells made of flexible silicone.

In the state of the art, all orthopaedic spacers and/or the related creation methods suffer some limitations and drawbacks.

In fact, the orthopaedic spacers made completely by hand by the orthopaedist have a significant limitation due to the low mechanical resistance and unpredictability of antibiotic release.

In the case of orthopaedic spacers made by specialist companies subsequently installed by the orthopaedist during the surgical operation it is observed that they suffer from poor use flexibility, in other words they are not sufficiently modular, therefore the orthopaedist is forced to make use of orthopaedic spacers of various sizes and shapes in order to face the different solution requirements during the operation.

An object of the present invention is to solve the problems encountered in the prior art by proposing a mould and forming accessories of an orthopaedic spacer compatible with medical cement and that allows its easy use.

In particular, it is an object of the present invention to provide a mould for the forming of a modular orthopaedic spacer that allows good compatibility with the anatomic structures affected by replicating their functions.

A further object of the present invention is to provide a mould for the forming of an orthopaedic spacer that is compatible with the materials and medical substances used, for example, antibiotics and the like for assisting with the care of prosthetic infections.

The dependent claims correspond to possible embodiments of the invention.

BRIEF DESCRIPTION OF THE DRAWINGS

This description is provided with reference to the accompanying figures, which are also provided purely by way of illustrative and thus non-limiting example, of which.

DESCRIPTION OF THE INVENTION

In the accompanying FIGS. 1-6, reference number 1 indicates a forming mould of an an orthopaedic temporary spacer made of medical cement in some preferred embodiments, in accordance with the present invention.

In detail, but not limiting for the present invention, the medical cement is a bone cement with an acrylic base that may be composed of two components, i.e. a powder with a liquid.

The powder component is generally composed of PMMA (polymethylmethacrylate) together with barium sulphate and various antibiotic(s).

The liquid component of the cement is generally composed of MMA (methyl methacrylate) together with DMPT (dimethyl-p-toluidine) and hydroquinone (HQ).

With reference to the accompanying figures, the mould 1 for forming the orthopaedic temporary spacer according to the present invention is such as to define a moulding cavity 2 delimited by a moulding surface 3. The mould 1 in accordance with the invention once filled with the pre-established medical cement is pressed by a specialist technician using a reusable medical press, not illustrated or described below since not being part of the present invention. In other words, the forming mould 1 according to the present invention is suitable for being pressed via a reusable medical press not illustrated in the accompanying figures.

The mould 1 has at least one hole 4 and/or a supply conduit through which the medical cement is introduced during the creation of an orthopaedic temporary spacer.

In other words, the moulding cavity 2 is filled with the medical cement that is introduced by a specialist technician, for example an orthopaedic physician.

The introduction of the medical cement into the mould 1 can take place through a manual dispenser or a controlled nozzle from which the cement paste already dosed with other substances exits, such as, for example, antibiotics and the like.

The mould 1 has at least one vent conduit which promotes the insertion and distribution of the medical cement into the moulding cavity 2 preventing the formation of air bubbles and/or empty spaces in the mould 1.

Preferably, the vent conduit comprises a containment tank 5a at one end that is open to the outside. The containment tank 5a is configured to control the correct flow of bone cement in an operating condition for the forming of an orthopaedic temporary spacer through the mould 1. The containment tank 5a is further configured to allow specialist personnel to check the correct polymerisation of the bone cement in an operating condition for forming an orthopaedic temporary spacer.

Figure 1:
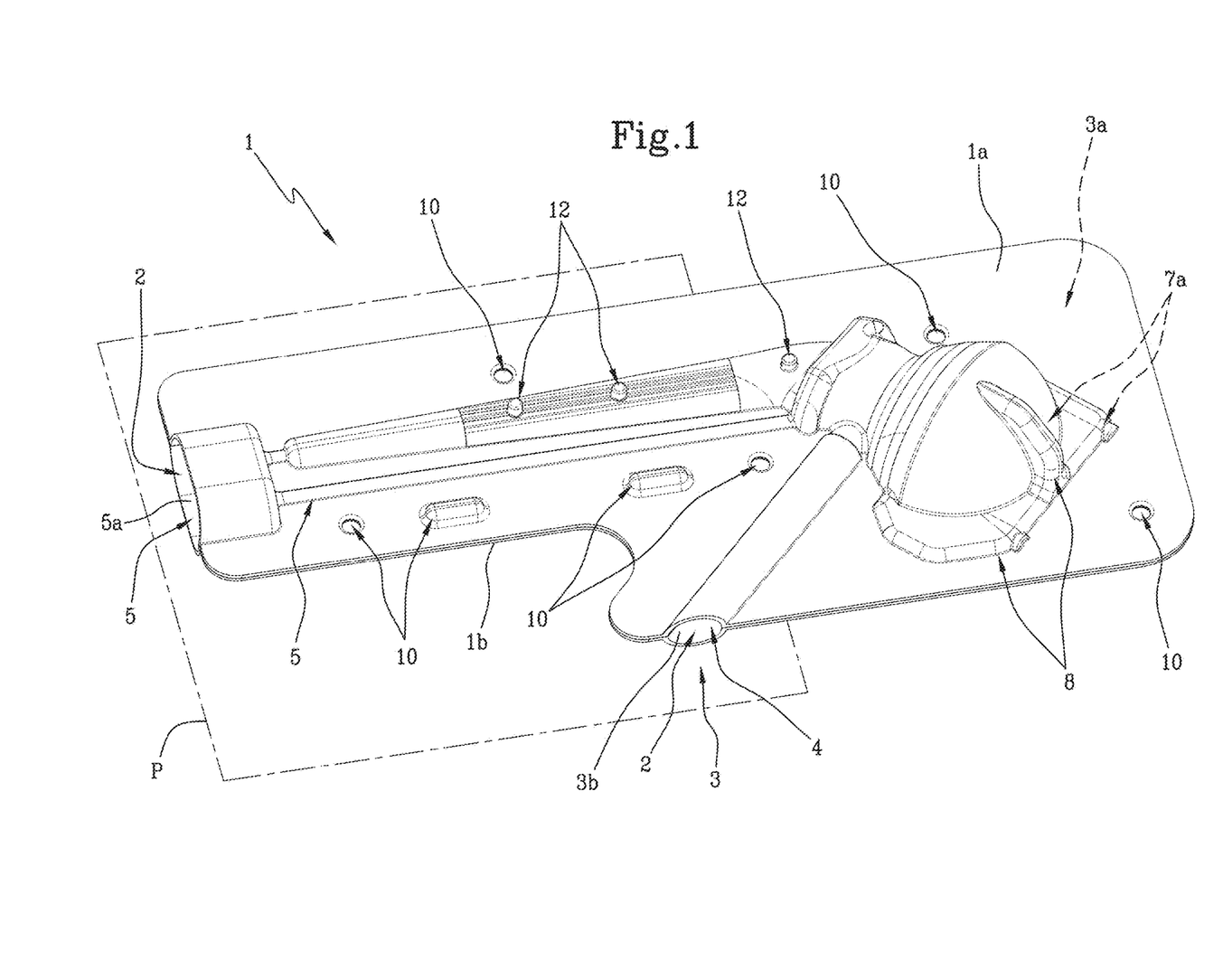
FIG. 1 is a perspective view of a forming mould according to the present invention.
Figure 2:
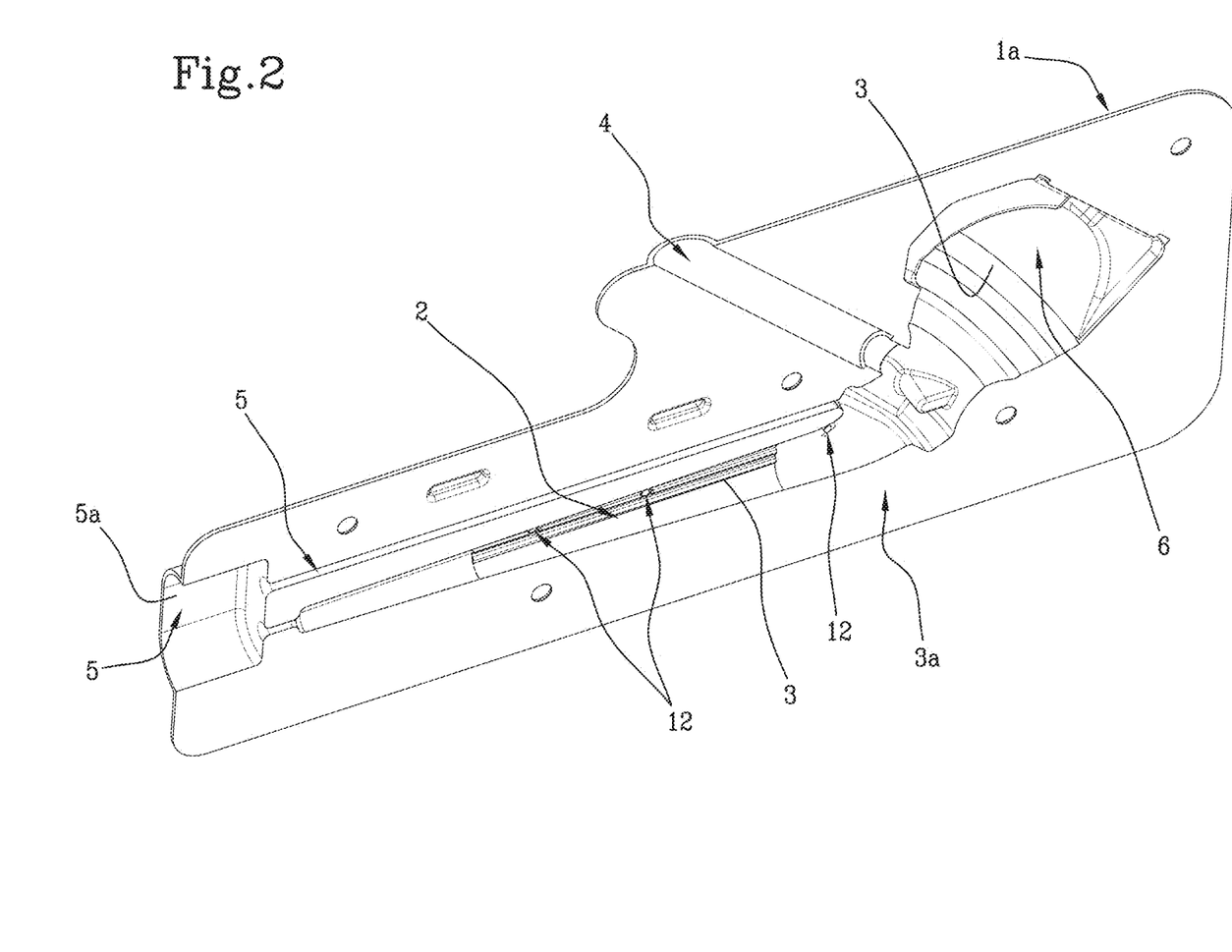
FIG. 2 is a perspective view of the mould of FIG. 1 with a part hidden for illustrating better the details of the mould otherwise not visible.

In accordance with the invention, with reference to the accompanying FIGS. 1 and 2, the mould 1 comprises a first moulding element 1a and a second moulding element 1b which can be coupled to one another to define the forming mould 1 itself.

Preferably, the first moulding element 1a and the second moulding element 1b comprise a first portion 3a of the moulding surface 3 and a second portion 3b of the moulding surface 3, respectively. In FIG. 2, which only shows by way of example the second moulding element 1b, it is possible to identify the aforementioned moulding surface 3, in particular the second portion 3b of the moulding surface 3.

The moulding surface 3 is configured to impart a pre-established shape on the medical cement and to create the orthopaedic spacer. It is therefore comprehensible that the shape of the moulding surface 3, visible in the accompanying figures, is a negative reproduction of what will be the external outline of the orthopaedic temporary spacer once the medical cement has set.

Advantageously, the mould 1 has at least one sector 6 such as to define at least one portion of the moulding surface 3 and wherein such sector 6 is made of a copolymer-based material and/or thermoplastic polymer.

In other words, at least one portion of the moulding surface 3 of the mould 1 for the forming of an orthopaedic temporary spacer is made, at least in one sector 6, with a thermoplastic copolymer-based material.

Preferably, the aforementioned sector 6 is defined by the first moulding element 1a and is made with a thermoplastic copolymer-based material.

Preferably, the first moulding element 1a, therefore the sector 6, is made of a TPE-SEBS (thermoplastic elastomer—styrene ethylene butylene styrene) based material, even more preferably the first moulding element 1a is made of TPE-SEBS.

Preferably, the second moulding element 1b is made of a polypropylene-based material, even more preferably the second moulding element 1b is made of semi-rigid polypropylene.

In accordance with the invention, the opposite situation between the two moulding elements 1a and 1 b is also comprised, wherein the second moulding element 1b is made of a TPE-SEBS based material and the first moulding element 1a is made of a polypropylene-based material. Preferably, the second moulding element 1b is made of a TPE-SEBS based material and the first moulding element 1a is made of semi-rigid polypropylene.

In accordance with the invention, also in the case in which the forming mould 1 has an internally hollow single body such as to determine the moulding cavity 2 delimited by a moulding surface 3, at least one sector 6 of the moulding surface 3 is made with a thermoplastic copolymer-based material, preferably it is made of TPE-SEBS. The embodiment described above is not illustrated in the accompanying figures but is however easily deducible by observing the mould 1 illustrated by way of example in the accompanying FIG. 1 with the first moulding element 1a and the second moulding element 1b still coupled to one another.

In the embodiment in question, the first moulding element 1a and said second moulding element 1b have their respective first moulding surface 3a and second moulding surface 3b specularly equal to one another with respect to a coupling plane "P".

By way of non-limiting example, the forming mould 1 illustrated in FIGS. 1 and 2 is preferably a mould 1 for creating orthopaedic spacers intended for a hip or a shoulder of a patient.

Figure 4A:
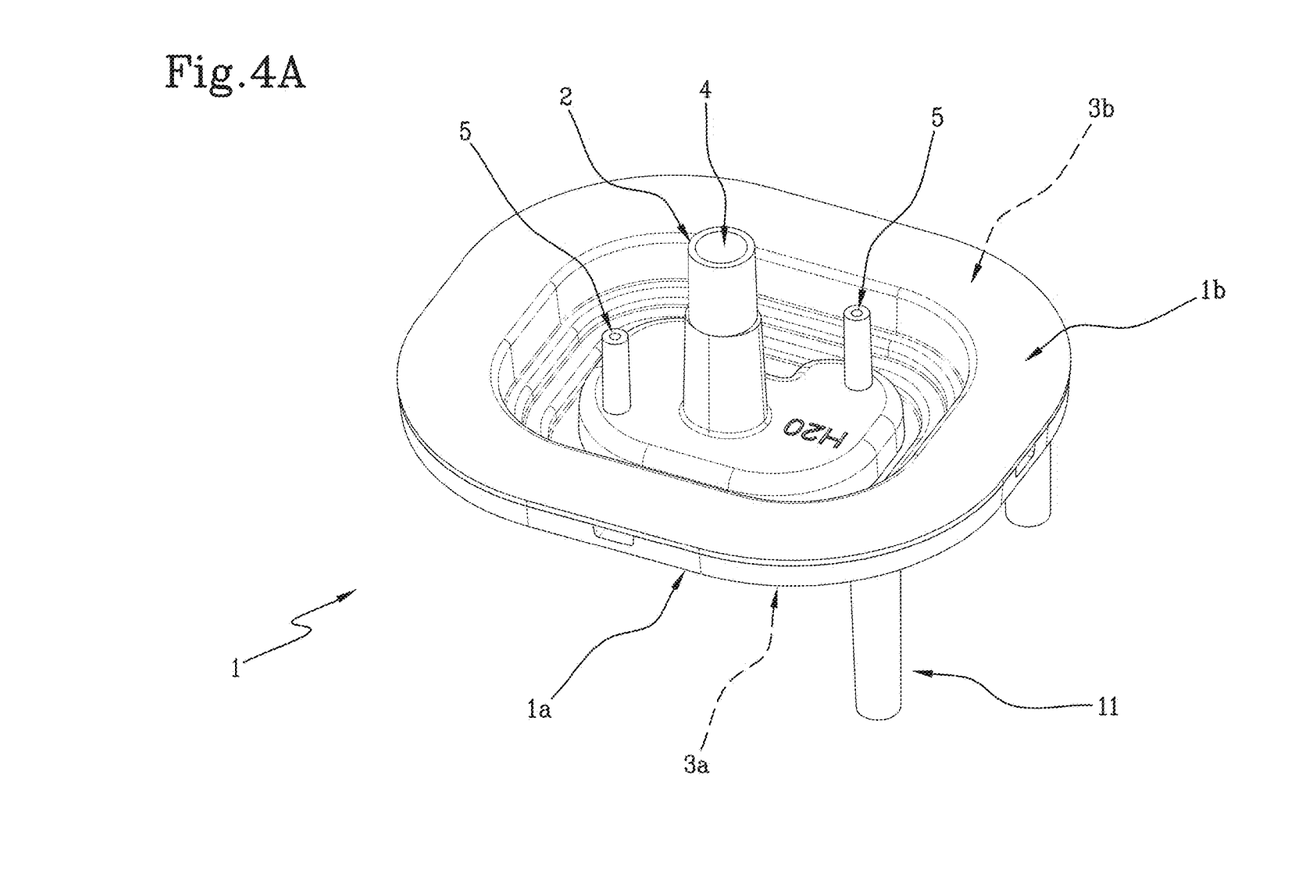
FIG. 4A is a perspective sectional view of a different embodiment of a mould in accordance with the present invention.
Figure 4B:
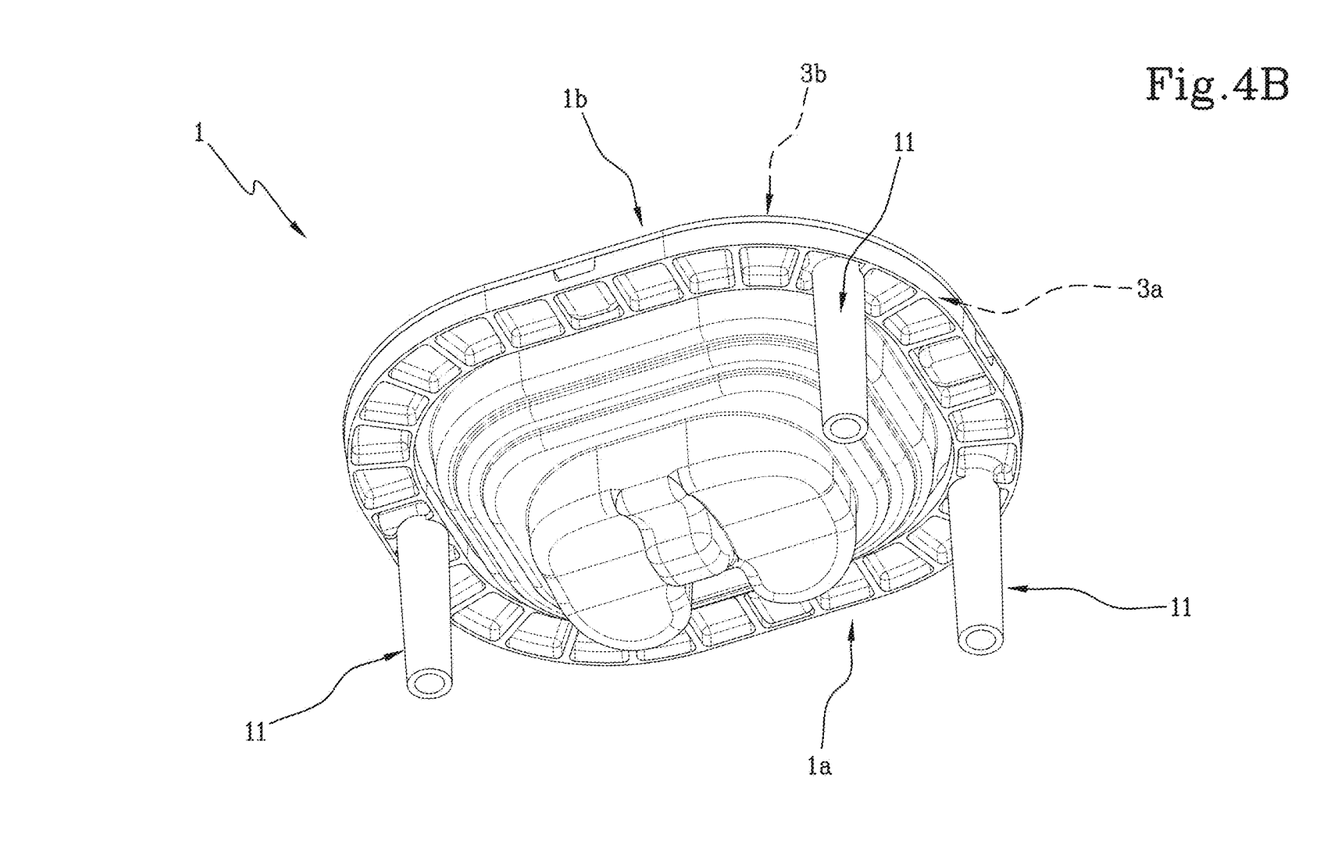
FIG. 4B is a perspective sectional view of the mould of FIG. 4A.

In a different embodiment of the invention, illustrated by way of non-limiting example in the appended FIGS. 4A-4B, the mould 1 is configured so as to create an orthopaedic temporary spacer intended for a tibial implant of a patient's knee. The mould 1 for creating the tibial spacer schematically depicted in FIGS. 4A and 4B is represented in the closed configuration, i.e. with the first moulding element 1a and the second moulding element 1b coupled to one another.

In the specific case, the first moulding surface 3a of the first moulding element 1a has a concave shape adapted to contain a portion of the medical cement and the second moulding surface 3b of the second moulding element 1b has a suitable shape to be inserted (to be coupled) at least partially into the first moulding surface 3a for imparting a pre-established shape onto the orthopaedic temporary spacer.

Also in this embodiment, at least the first moulding element 1a is made with a thermoplastic copolymer-based material, preferably it is made of TPE-SEBS.

Preferably, the second moulding element 1b is made of a polypropylene based material. Preferably, the second moulding element 1b is made of a semi-rigid polypropylene material.

In other words, the second moulding element 1b is a piston, not necessarily cylindrical, made of semi-rigid polypropylene insertable in a concave portion of the first moulding element 1a, a container precisely made of TPE-SEBS, so as to compress and compact the medical cement for making the orthopaedic temporary spacer insertable in the knee joint.

In accordance with the invention, the opposite configuration between the two moulding elements 1a and 1 b is also comprised, where the first moulding element 1a is made of a polypropylene based material and the second moulding element 1b is made of a TPE-SEBS based material. Also in the embodiment described herein there is at least one vent conduit 5, preferably at least two vent conduits 5 to allow the correct flow and distribution of the bone cement into the mould 1 in an operating configuration for forming the orthopaedic spacer in question. As already mentioned, the vent conduits 5 also have the function of facilitating the correct polymerisation of the bone cement introduced into the closed mould 1. Preferably, the second moulding element 1b, the piston, is made of TPE-SEBS, whereas the first moulding element 1a, the medical cement container element, is made of semi-rigid polypropylene.

As illustrated schematically in the accompanying FIG. 4B, the mould 1 at the first moulding element 1a has support stems 11 to allow the correct positioning of the mould 1 on a work surface in a forming configuration of the spacer.

Figure 5A:
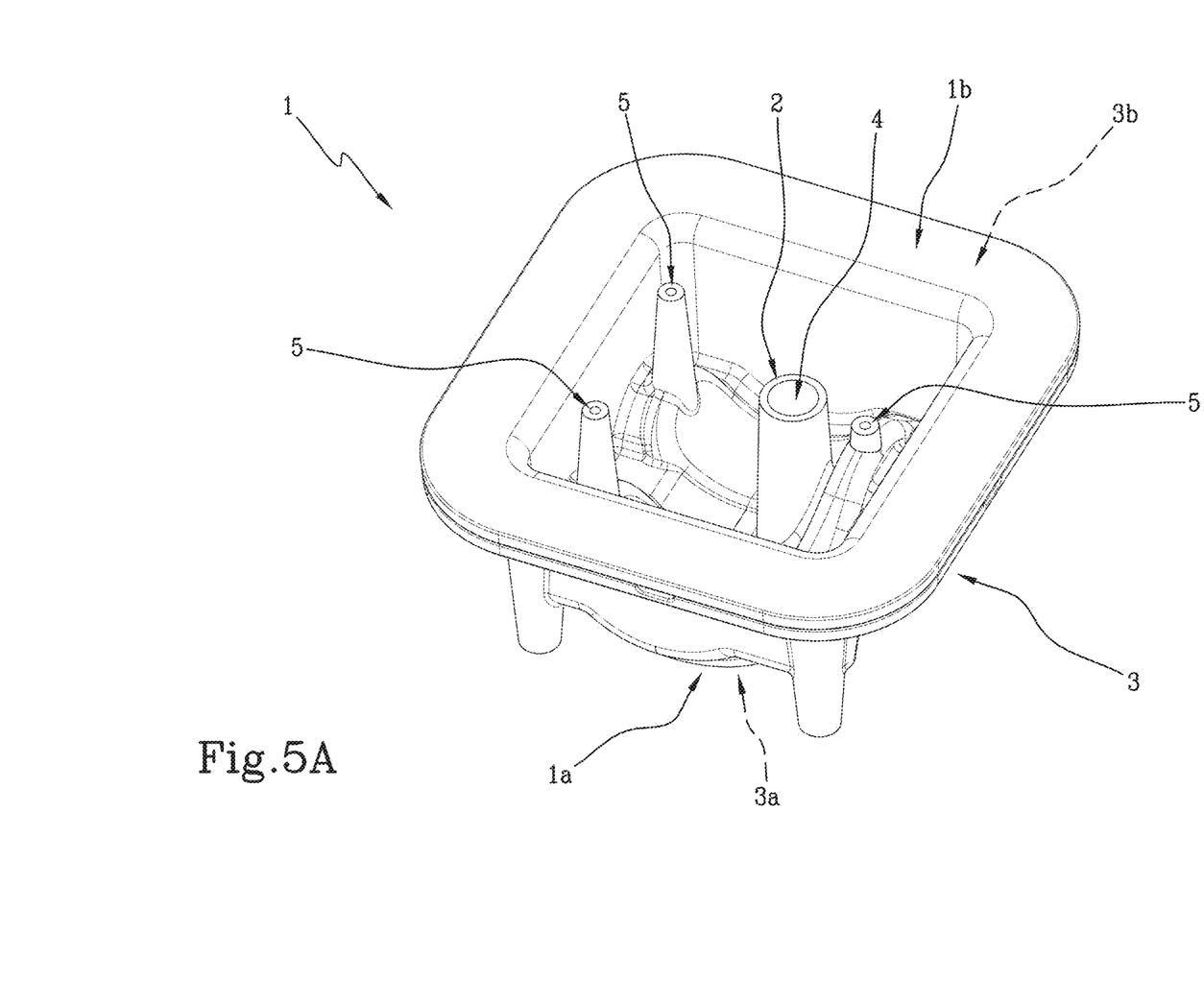
FIG. 5A is a further perspective sectional view of a further and different embodiment of a mould in accordance with the present invention.
Figure 5B:
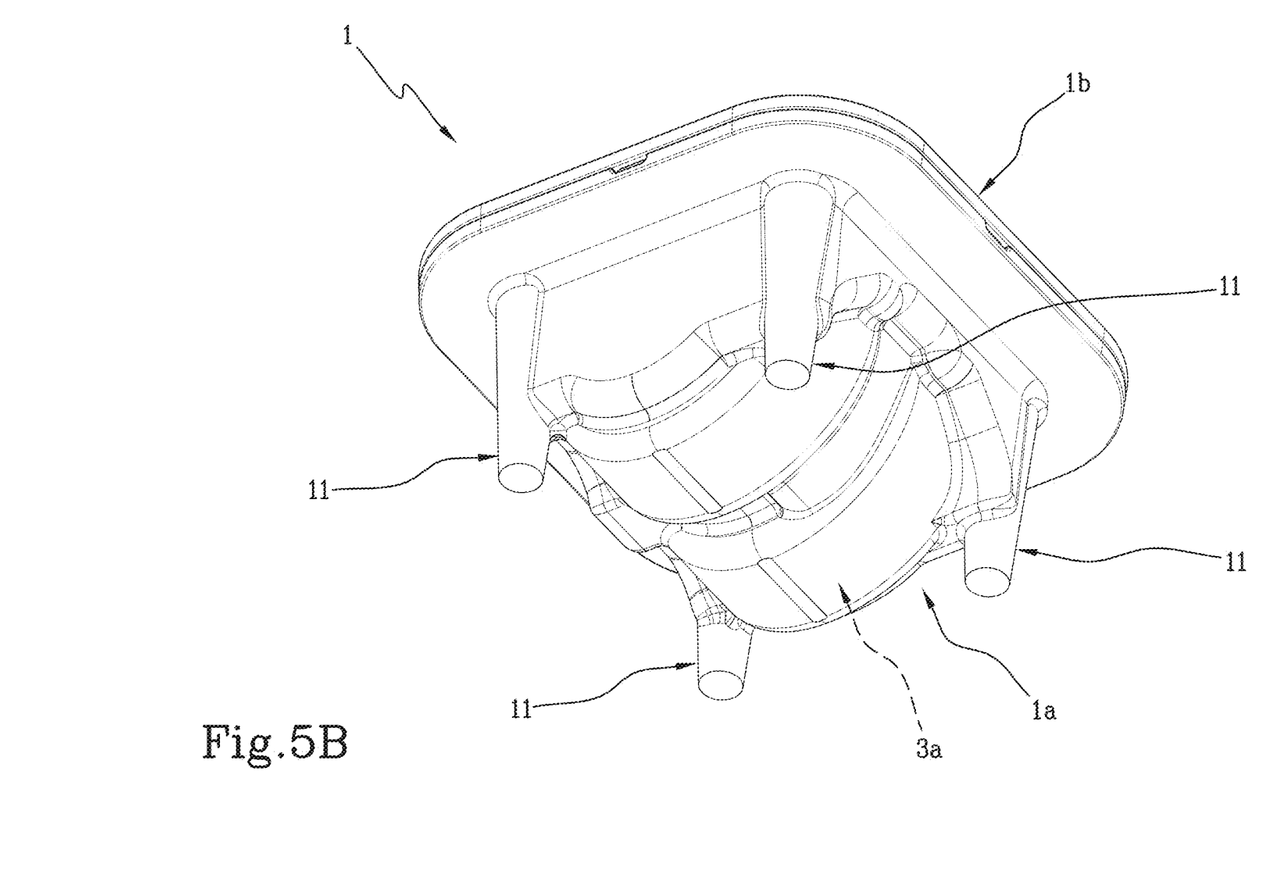
FIG. 5B is a further perspective sectional view of the mould of FIG. 5A.
Figure 6:
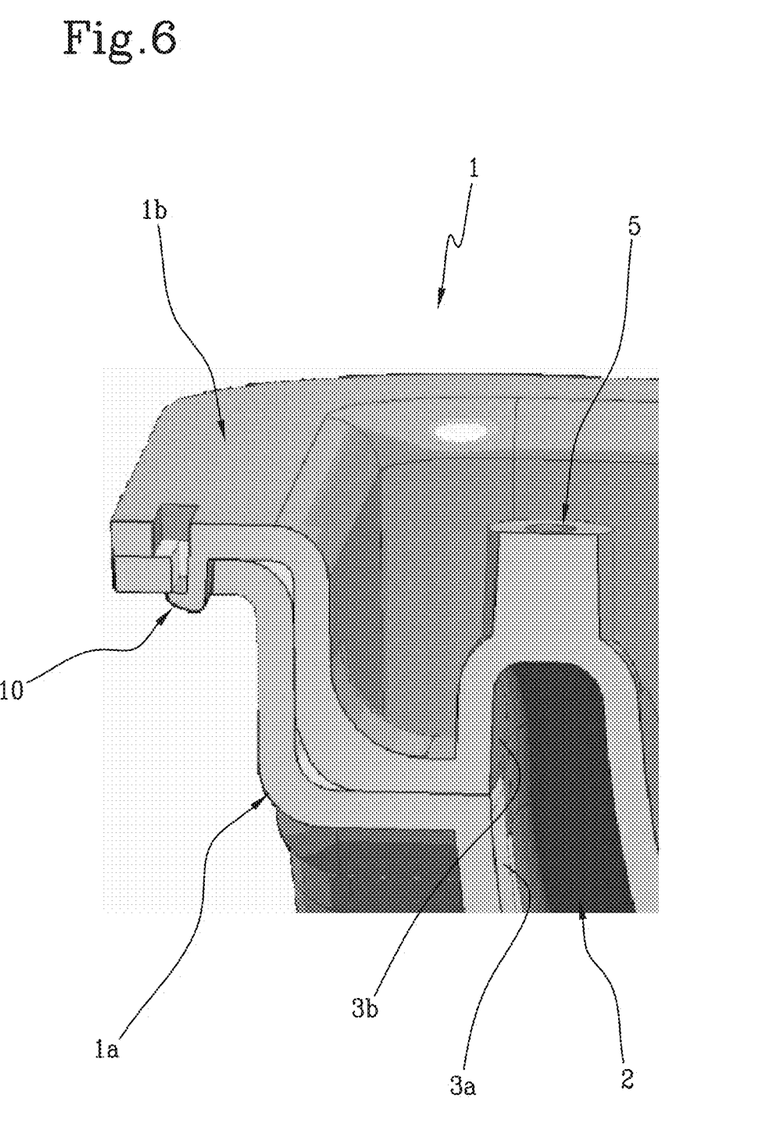
FIG. 6 is a sectional view of a detail of the mould of FIG. 5A.

With reference to the accompanying FIGS. 5A-5B, by way of non-limiting example, a further and different embodiment of the invention is illustrated referring to a mould 1 configured so as to create an orthopaedic temporary spacer intended for a femoral implant of a knee joint.

The mould 1 for creating the femoral spacer schematically depicted in FIGS. 5A and 5B is represented in the closed configuration, i.e. with the first moulding element 1a and the second moulding element 1b coupled to one another, for example in a configuration predisposed for the insertion of the moulding bone cement.

In accordance with the invention, also in this case, the mould 1 comprises a first moulding element 1a and a second moulding element 1b which can be coupled to one another to define the forming mould 1 itself.

In the specific case the first moulding element 1a and the second moulding element 1b are internally hollow and are configured to be superimposed on top of one another at an open central portion and such as to define a containment volume for the medical cement through respective internal cavities respectively defining the first moulding surface 3a and the second moulding surface 3b.

The orthopaedic spacer formed through the coupling of the first moulding element 1a and the second moulding element 1b is preferably in the shape of a horseshoe. In fact, from FIGS. 5A and 5B it is possible to note the fact that the mould 1 has two vent conduits 5 at the free ends of the horseshoe shaped orthopaedic spacer and a central vent conduit 5, preferably at the arched portion of the orthopaedic temporary spacer in question.

In accordance with the invention, the first moulding element 1a or the second moulding element 1b have a passage hole 4, or a conduit, for allowing the passage of a portion of medical cement for creating the orthopaedic temporary spacer. Also in this embodiment, at least the first moulding element 1a is made with a thermoplastic copolymer-based material, preferably it is made with a TPE-SEBS based material.

Preferably, the second moulding element 1b is made of a polypropylene-based material, even more preferably the second moulding element 1b is made of semi-rigid polypropylene.

In accordance with the invention, the opposite situation between the two moulding elements 1a and 1b is also comprised in this specific case, where the second moulding element 1b is made of a TPE-SEBS based material and the first moulding element 1a is made of a polypropylene based material. Preferably, the second moulding element 1b is made of a TPE-SEBS based material and the first moulding element 1a is made of semi-rigid polypropylene.

As illustrated schematically in the appended FIG. 5B, the mould 1 at the first moulding element 1a has support stems 11 to allow the correct positioning of the mould 1 on a work surface in a forming configuration of the orthopaedic temporary spacer.

In a further and different embodiment of the invention included in the inventive concept of the invention, the sector 6 is a forming insert 6a adapted to be inserted in the moulding cavity 2 of the forming mould 1; the first moulding element 1 and the second moulding element 1b can still be coupled for defining the forming mould 1, as mentioned above. By way of non-limiting example, a forming insert 6a is illustrated in the accompanying FIGS. 3A and 3B.

Figure 3A:
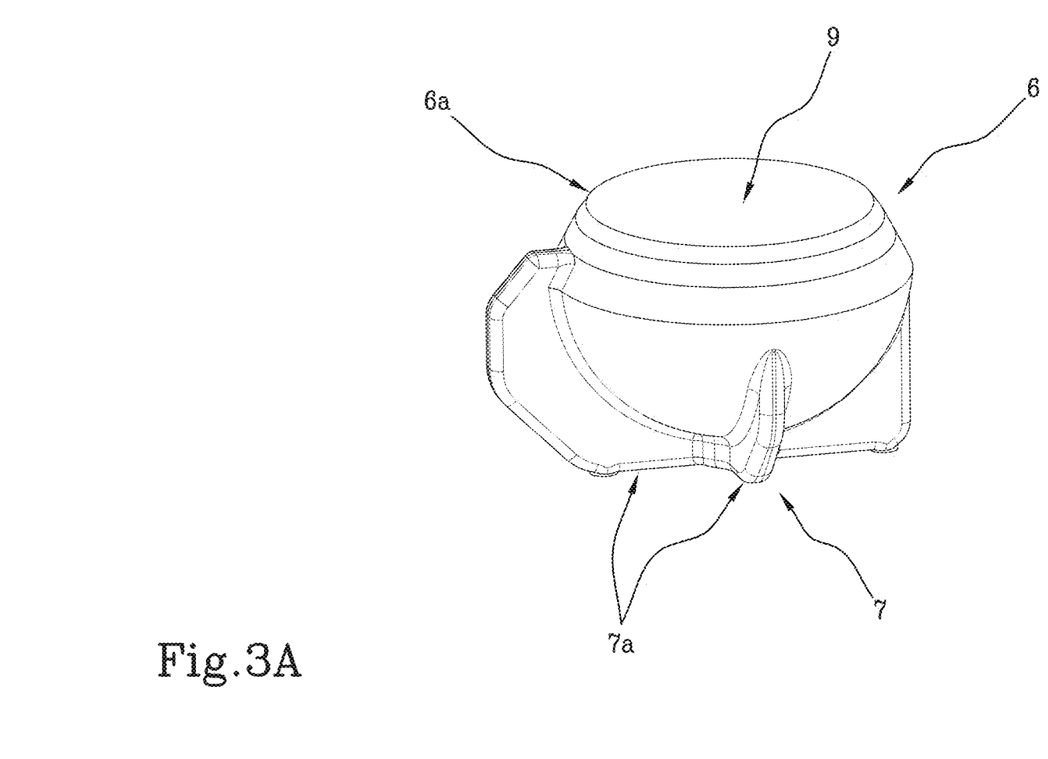
FIG. 3A is a perspective view of a detail of the mould of FIG. 1, with several parts hidden so as to highlight others otherwise not visible.
Figure 3B:
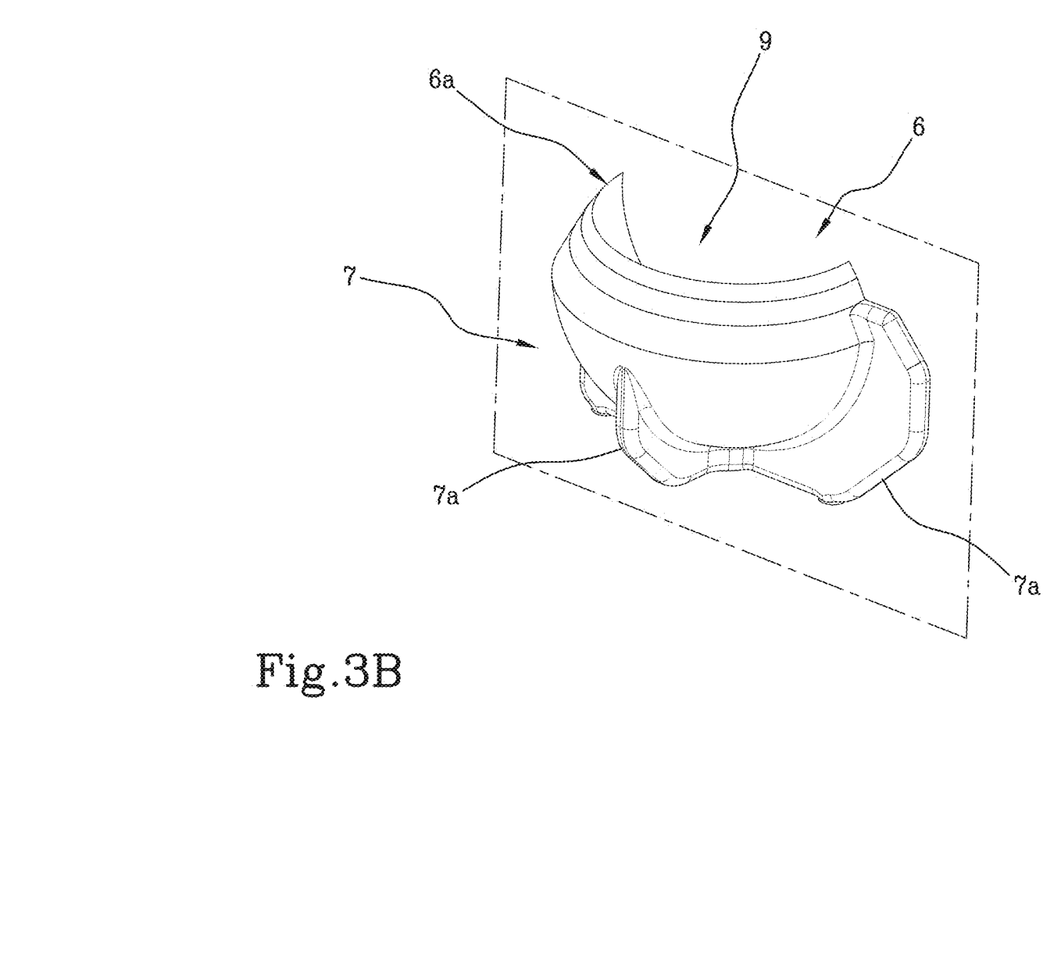
FIG. 3B is a perspective sectional view of the detail of FIG. 2A.

In particular, the mould 1 comprises the first moulding element 1a and the second moulding element 1b and wherein the forming insert 6a is operatively associated with the first moulding element 1a and/or the second moulding element 1b and configured to impart a pre-established shape to a further portion of medical cement and create the orthopaedic temporary spacer in question.

Advantageously, the forming insert 6a is made with a thermoplastic copolymer-based material, preferably it is made with a TPE-SEBS based material. Preferably, the forming insert 6a is made of TPE-SEBS.

In the specific case, the first moulding element 1a and/or the second moulding element 1b are made with a polypropylene based material. Preferably, the first moulding element 1a and the second moulding element 1b are made of polypropylene.

The forming insert 6a is configured to be operatively included between the first moulding surface 3a and the second moulding surface 3b in an operating condition for forming a portion of medical cement for creating the orthopaedic temporary spacer in question.

Preferably, the forming insert 6a comprises positioning means 7 for facilitating and accelerating the manoeuvres of the specialist technician during the creation of the orthopaedic temporary spacer without making any positioning errors of the insert 6 within the mould 1.

In particular, the forming insert 6a has a pair of ribs 7a in relief on an outer surface thereof adapted to be operatively inserted into respective shaped portions 8 of the first moulding element 1 and/or the second moulding element 1b.

Furthermore, the appointed operator, like the orthopaedic physician, does not run the risk of making any errors in the arrangement of the forming insert 6a. In fact, the ribs 7a and respective shaped portions 8, have a different outline and/or size so as to make the positioning of the insert 6a in the mould 1 unequivocal and not invertible.

Preferably, the forming insert 6a has a shaped surface 9 having a concave spherical cap shape configured to impart a respective convex spherical cap shape to a portion of medical cement in an operating condition for the forming of a portion of medical cement for creating the orthopaedic temporary spacer.

FIG. 3A schematically illustrates with reference number 9 the above-mentioned concave spherical cap 9; in FIG. 3B it is possible to see the curvature given that the forming insert 6a is illustrated cut along a plane of symmetry.

The forming insert 1 comprises coupling means 10 configured to join the first moulding element 1a and the second moulding element 1b in an operating condition for forming a portion of medical cement for creating the orthopaedic temporary spacer in question.

Preferably, the coupling means 10 are also configured to determine a pre-established position between the first moulding element 1a and the second moulding element 1b in an operating condition for forming a portion of medical cement.

Preferably, the coupling means 10 comprise clamping means and/or portions shaped to be coupled by jointing or superposition so as to correctly position the first moulding element 1a with the second moulding element 1b for coupling. A non-limiting example of the coupling means 10 is schematically illustrated in the sectional view of the accompanying FIG. 6, wherein a snap closing system of the mould 1 is highlighted for creating the orthopaedic temporary spacer intended for a femoral implant of a knee joint.

In accordance with the invention, the forming mould 1 preferably comprises centring elements 12, as illustrated by way of non-limiting example in FIGS. 1 and 2.

The centring elements 12 may be distributed in various points of the moulding elements 1a, 1b and allow the correct positioning of any inserts made of metal or another material for consolidation together with the bone cement for creating the orthopaedic temporary spacer with metal reinforcement. In other words, the mould 1 according to the present invention, regardless of the embodiments described above and illustrated in the appended figures, may comprise centring elements 12 configured for positioning any reinforcements made of metal or another material in a pre-established point, which must be included in the orthopaedic temporary spacer.

In accordance with the invention, the forming mould 1 is a mould that can be reused through a reversible coupling, for example, between the first moulding element 1a and the second moulding element 1b. Also in the case of the embodiment in which the forming mould 1 has a single body, the mould 1 is reusable in accordance with any health and hygiene standards in force.

In accordance with the invention, the forming mould 1 may also be of the disposable type, therefore not reusable. Hence neither the first moulding element 1a nor the second moulding element 1b, where envisaged, nor the forming insert 6a, can be used for more than one moulding.

The present invention achieves the intended aims.

Advantageously, the present invention provides a forming mould for orthopaedic temporary spacers which is made of non-toxic materials and that are compatible with all types of medical substances and formulae of bone cement used for making the spacer. In particular, the mould according to the present invention is made with flexible, bio-compatible materials, equipped with substantial flexibility and that are inert with any antibiotics introduced into the forming medical cement.

Advantageously, the present invention provides a simple and practical forming mould, which is quick to prepare and intuitive to use.

Advantageously, the present invention provides a modular forming mould for an orthopaedic temporary spacer that does not release foreign substances into the medical cement used for the forming of the spacer itself.

The invention claimed is:

1. A forming mould (1) for use in the forming of an orthopedic modular spacer made of a medical cement, which defines a moulding cavity (2) delimited by a moulding surface (3), which moulding surface is configured for imparting a pre-determined shape to said medical cement and realize said orthopedic spacer, in which at least one sector (6) of said forming mould (1) defining at least one portion of said moulding surface (3), is made of a copolymer-based material and/or a thermoplastic polymer, wherein said sector (6) is a forming insert (6a) suitable for being inserted into said moulding cavity (2) of the forming mould (1), the forming mould (1) further comprising a first moulding element (1a) and a second moulding element (1b), and in which said forming insert (6a) is operatively associated to said first moulding element (1a) and/or said second moulding element (1b), and configured for imparting a pre-established shape to a further portion of said medical cement and said orthopedic spacer.

2. A forming mould (1) in accordance with claim 1, wherein said first moulding element (1a) and said second moulding element (1b) respectively, comprise a first portion (3a) of the moulding surface (3) and a second portion (3b) of the moulding surface (3); said sector (6) being defined by said first moulding element (1a) realized with the copolymer-based material and/or the thermoplastic polymer.

3. A forming mould (1) in accordance with claim 2, wherein said first moulding element (1a) is made of a TPE-SEBS based material.

4. A forming mould (1) in accordance with claim 2, in which said first portion (3a) of the first moulding element (1a) exhibits a concave shape, which is suitable to contain a portion of said medical cement, and said second portion (3b) of the second moulding element (1b) exhibits a shape suitable to be inserted at least partially into said first portion (3a) in order that a pre-established shape is imparted to said orthopedic spacer.

5. A forming mould (1) in accordance with claim 4, wherein said second moulding element (1b) is made of a polypropylene-based material.

6. A forming mould (1) in accordance with claim 2, in which the first moulding element (1a) and the second moulding element (1b) are internally hollow and exhibit a cross section in the shape of a horseshoe and are configured for being stacked one on the other at an open side portion, and such as to define a containment volume of said medical cement via respective internal cavities, which respectively define a first moulding surface and second moulding surface, said first moulding element (1a) or said second moulding element (1b) exhibiting a passage hole (4) in order to allow passage of a portion of said medical cement for obtaining said orthopedic spacer.

7. A forming mould (1) in accordance with claim 6, wherein said second mould element (1b) is made of a TPE-SEBS-based material.

8. A forming mould (1) in accordance with claim 1, wherein said forming insert (6a) is made of a TPE-SEBS-based material.

9. A forming mould (1) in accordance with claim 1, wherein said first moulding element (1a) and/or said second moulding element (1b) are made of a polypropylene-based material.

10. A forming mould (1) in accordance with claim 1, wherein said forming insert (6a) is configured for being operatively included between said first moulding surface (3a) and said second moulding surface (3b) in an operative condition of forming a medical cement portion for obtaining said orthopedic spacer.

11. A forming mould (1) in accordance with claim 1 in which said forming insert (6a) comprises positioning means (7), said positioning means (7) comprising at least a pair of ribs (7a) in relief on an outer surface of said forming insert (6a), said pair of ribs (7a) being adapted to be operatively inserted into respective shaped portions (8) of said first moulding element (1a) or second moulding element (1b).

12. A forming mould (1) in accordance with claim 1, in which said forming insert (6a) exhibit a shaped surface (9) having a concave spherical cap form, configured for imparting a respective convex spherical cap form to a medical cement portion in an operative condition of forming a medical cement portion in order to obtain the orthopedic spacer.

13. A forming mould (1) in accordance with claim 2, wherein said first moulding element (1a) and said second moulding element (1b) can be coupled in order to define said forming mould (1).

14. A forming mould (1) in accordance with claim 1, wherein said first moulding element (1a) and said second moulding element (1b) can be coupled in order to define said forming mould (1).

15. A forming mould (1) according to claim 3, wherein said first moulding element (1a) is made of TPE-SEBS.

16. A forming mould (1) according to claim 4, wherein said orthopedic spacer is a spacer configured for a tibial implant of a knee.

17. A forming mould (1) according to claim 6, wherein said orthopedic spacer is a spacer configured for a knee femoral implant.

18. A forming mould (1) according to claim 7, wherein said second moulding element (1b) is made of TPE-SEBS.

19. A forming mould (1) according to claim 8, wherein said forming insert is made of TPE-SEBS.

20. A forming mould (1) according to claim 9, wherein said first moulding element (1a) and said second moulding element (1b) are made of polypropylene.

* * * * *